(12) United States Patent
Duis et al.

(10) Patent No.: US 10,987,482 B1
(45) Date of Patent: Apr. 27, 2021

(54) PATIENT VALVE FOR USE WITH MANUAL RESUSCITATOR

(71) Applicant: Ventlab, LLC, Grand Rapids, MI (US)

(72) Inventors: Ronald Duis, Allegan, MI (US); Mark Zyzelewski, Kalamazoo, MI (US); Daniel Bowen, Grand Rapids, MI (US)

(73) Assignee: Ventlab, LLC, Grand Rapids, MI (US)

( * ) Notice: Subject to any disclaimer, the term of this patent is extended or adjusted under 35 U.S.C. 154(b) by 730 days.

(21) Appl. No.: 15/341,805

(22) Filed: Nov. 2, 2016

(51) Int. Cl.
*A61M 16/20* (2006.01)
*A61M 16/00* (2006.01)
*A61M 16/06* (2006.01)

(52) U.S. Cl.
CPC ...... *A61M 16/208* (2013.01); *A61M 16/0078* (2013.01); *A61M 16/06* (2013.01); *A61M 2016/0027* (2013.01); *A61M 2205/583* (2013.01); *A61M 2207/00* (2013.01)

(58) Field of Classification Search
CPC ............ A61M 16/208; A61M 16/0078; A61M 2016/0027; A61M 16/06; A61M 2207/00; A61M 2205/583
See application file for complete search history.

(56) References Cited

U.S. PATENT DOCUMENTS

| | | | |
|---|---|---|---|
| 5,103,854 A * | 4/1992 | Bailey | A61M 16/208 128/205.24 |
| 5,557,049 A | 9/1996 | Ratner | |
| 7,051,596 B1 | 5/2006 | Lau et al. | |
| 7,357,033 B2 * | 4/2008 | Lau | A61M 16/0078 73/736 |
| 7,464,601 B2 | 12/2008 | Grane et al. | |
| 8,211,128 B1 * | 7/2012 | Facundus | A61B 17/1114 128/898 |
| 8,522,618 B1 | 9/2013 | Ratner | |
| 2008/0251003 A1 * | 10/2008 | Boston | G01F 1/22 116/276 |

* cited by examiner

*Primary Examiner* — Theodore J Stigell
(74) *Attorney, Agent, or Firm* — Frank M. Scutch, III

(57) ABSTRACT

A manual resuscitator apparatus having a patient valve includes a housing having a first port for connection to ventilator bag, a second port for connection to a patient mask and a third port for an atmospheric vent. An air channel is configured integrally within the interior of the housing and a manometer is used for receiving air from the air channel. Either a linear or dial manometer is formed as a portion of the housing so the clinician can read both patient inhalation pressure from the first port and patient exhalation pressure from the second port.

13 Claims, 10 Drawing Sheets

PATIENT VALVE FOR USE WITH MANUAL RESUSCITATOR

FIELD OF THE INVENTION

The present invention relates generally to manual resuscitator apparatus and more particularly to a patient valve used with a bag valve mask resuscitator.

BACKGROUND

A manual resuscitator is a device using positive pressure to inflate the lungs of an unconscious person who is not breathing. The resuscitator is used in order to keep the patient oxygenated and alive. There are three basic types for resuscitators, a manual version (also known as a bag valve mask) consisting of a mask and a large hand-squeezed plastic bulb using ambient air, or with supplemental oxygen from a high-pressure tank. The second type is the Expired Air or breath powered resuscitator. The third type is an oxygen powered resuscitator. This type of resuscitator is driven by pressurized gas delivered by a regulator, and can either be automatic or manually controlled. The most popular type of gas powered resuscitator are time cycled, volume constant ventilators. All modern resuscitation devices typically are required to deliver greater than 85% oxygen when a gas source is available.

Bag valve mask resuscitators was a further advancement in resuscitation. Introduced in the 1960s, this device allowed two rescuers to perform CPR and ventilation on a non-breathing patient with an acceptable chance of success. This type of resuscitation device includes a non-rebreathing valve to provide positive pressure for manual ventilation needed when a patient lacks respiratory drive during resuscitation involving oxygen or air. The bag valve mask resuscitator now mostly replaced the demand valve as the primary method of ventilation, largely due to concerns of potential over-inflation with the demand valve by untrained rescuers. The bag valve mask resuscitator, unlike the older version of the demand valve (all new models of demand valve now have pressure relief valves set at 60 cm of water to prevent accidental over inflation of the lungs), may have a "pressure relief" valve to prevent inflation at greater than 40 cm $H_2O$ (3.92 Kilo-pascals) pressure with the result being that it is generally more common in the pre-hospital setting than the demand valve. However, the demand valve remains popular with basic life support providers and in situations where conserving supplies of oxygen is of paramount importance. The demand valve, while less popular today than it was previously, still remains in service, albeit with important safety features added, including the addition of a pressure-relief valve to prevent over-inflation and the restriction of its flow to 40 liters a minute.

BRIEF DESCRIPTION OF THE FIGURES

The accompanying figures, where like reference numerals refer to identical or functionally similar elements throughout the separate views and which together with the detailed description below are incorporated in and form part of the specification, serve to further illustrate various embodiments and to explain various principles and advantages all in accordance with the present invention.

Figure 1:
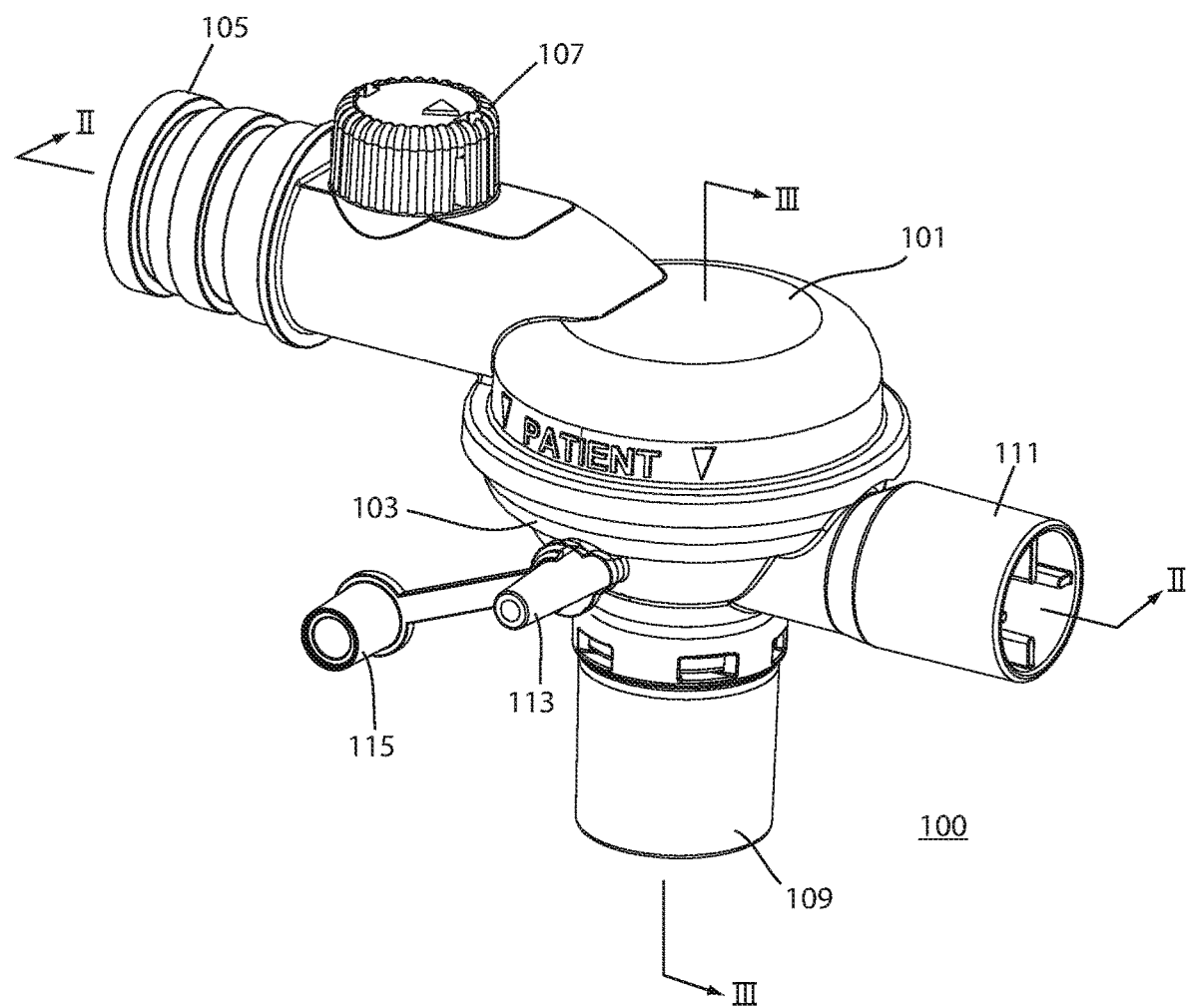
FIG. 1 is elevated perspective view of a patient valve with no manometer in accordance with an embodiment of the invention.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

DETAILED DESCRIPTION

Before describing in detail embodiments that are in accordance with the present invention, it should be observed that the embodiments reside primarily in combinations of method steps and apparatus components related to a patient valve for use with bag valve mask resuscitators. Accordingly, the apparatus components and method steps have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

In this document, relational terms such as first and second, top and bottom, and the like may be used solely to distinguish one entity or action from another entity or action without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element.

FIG. 1 is elevated perspective view of a patient valve with no manometer in accordance with an embodiment of the invention. The patient valve 100 includes a substantially circular upper housing 101 and lower housing 103. The upper housing 101 includes a bag port 105 used to connect to a ventilation bag. A pressure relief valve 107 includes a rotatable knob for controlling its position and is used for controlling the amount of inhalation pressure from the ventilation bag to the patient's lungs. The lower housing 103 is also substantially circular in shape and includes a rotating mask port 109 for directing inhalation air from a ventilation bag to a patient mask. An air expiratory port 111 allows exhalation air from the rotating mask port 109 to escape through this port to atmosphere. A side port 113 and port cap 115 are used to allow sampling or connection of a non-integrated manometer.

Figure 2:
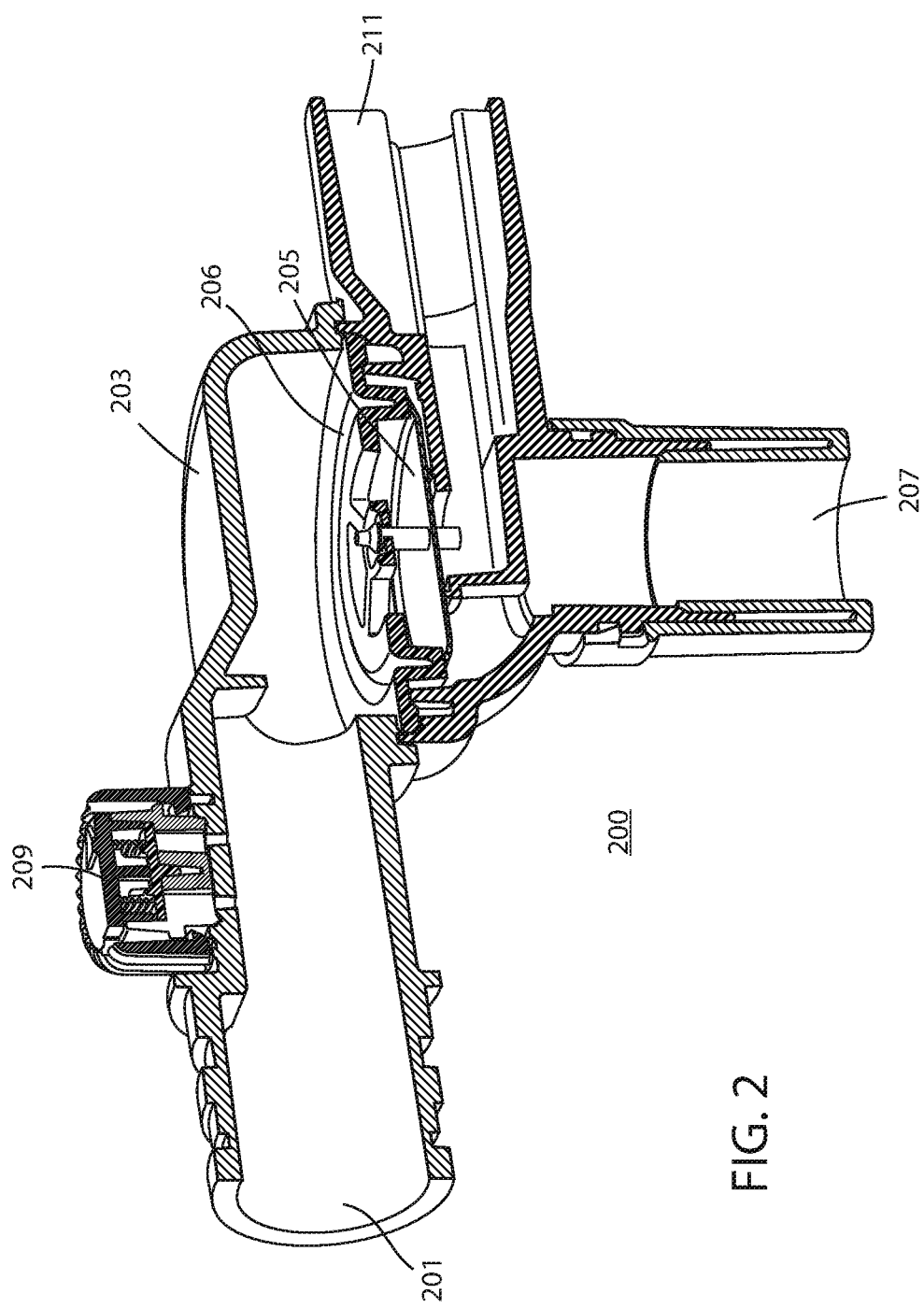
FIG. 2 is a cross-sectional view of the patient valve through lines II-II shown in FIG. 1.

FIG. 2 is a cross-sectional view of the patient valve shown through lines II-II of FIG. 1. The patient valve 200 shows an arrow illustrating air that would move from a ventilation bag through the bag port 201. During an inhalation breath cycle, the air moves from a ventilation bag through the upper housing 203. The patient valve 200 includes an umbrella valve 205 that is seated under and within a valve plate 206. Upon the application of an adequate amount of air pressure, the umbrella valve will flex to permit airflow to move downwardly and/or around the perimeter of the valve into the rotating mask port 207. The relief pressure valve 209 allows the clinician to adjust the valve to prevent inhalation overpressure. The pressure relief valve also serves to prevent barotrauma in healthy or compromised patients. During the exhalation cycle, the umbrella valve 205 prevents the patient's exhalation breath from moving into the upper housing 203 by directing the airflow through an air expiratory port 211.

Figure 3:
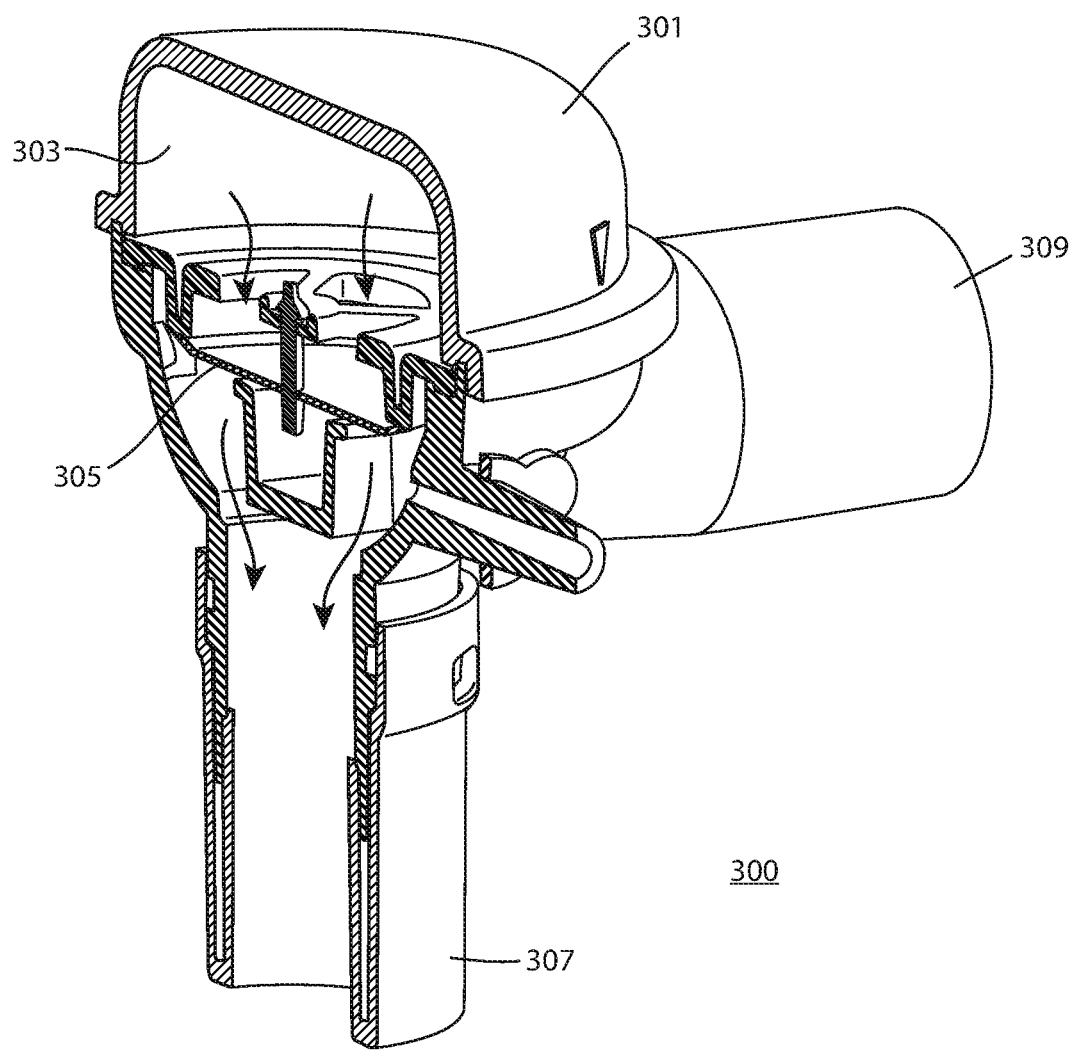
FIG. 3 is a cross-sectional view of the valve through lines III-III shown in FIG. 1.

FIG. 3 is a cross-sectional view of the valve shown through lines shown in FIG. 1. The patient valve 300 illustrates where the upper housing 301 directs air during the inhalation cycle from a ventilation bag port (not shown) though an inlet channel 303 past the umbrella valve 305 into the rotating mask port 307. During the exhalation cycle, air is moved back from the rotating mask port 307 where the umbrella valve flexes upward, allowing exhaled air to be directed into the air expiratory port 309.

Figure 4:
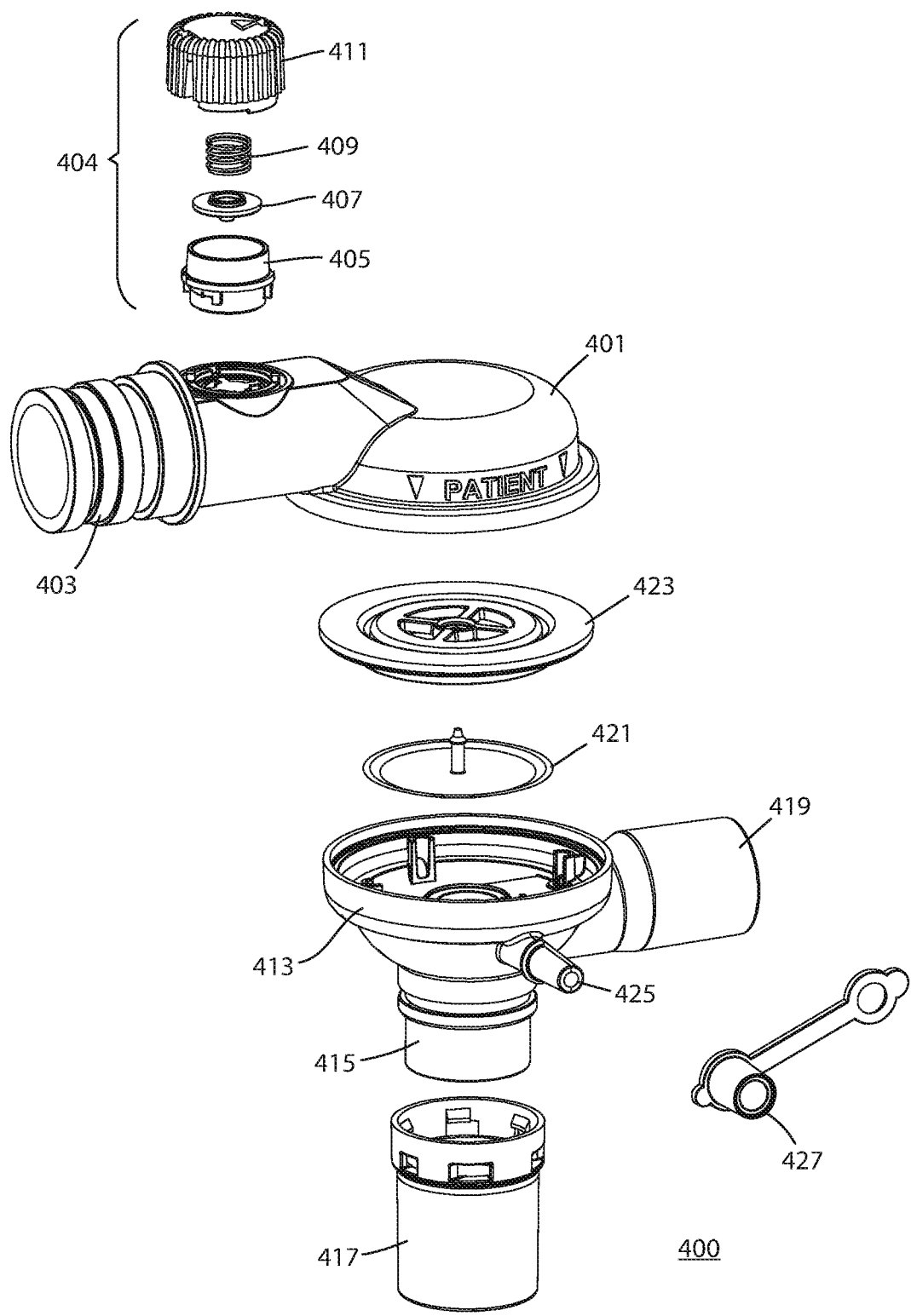
FIG. 4 is an exploded view of the patient valve with no manometer.

FIG. 4 is an exploded view of the patient valve with no manometer. The patient valve 400 includes a top or upper housing 401 that includes a bag port 403 extending therefrom. Positioned adjacent to the bag port 403 is a pressure relief valve 404 that is comprised of a pop off body 405, a pop off piston 407, a pop off spring 409 and a pop off cap 411. As described herein, the pressure relief valve 404 works to lower inhalation pressure in the event a lower pressure is required for an infant or adolescent patients. A lower housing 413 includes a mask port 415 that is used in combination with a rotating mask port component 417 for allowing a mask (not shown) to rotate separately from patient valve 400 relative to the patient's head and face. This allows for patient comfort as well as ease of use by the clinician. Further, an air expiratory port 419 is used for directing exhalation air from the patient mask out to the atmosphere.

In use, an umbrella valve 421 is seated below valve plate 423. The umbrella valve is substantially circular in shape and is made of a silicone or other flexible material so that will flex with air moving against it. The valve plate 423 is configured to fit within the top portion of the lower housing 413. When assembled, during the inhalation cycle, when air is forced though the ventilation bag port 403, the umbrella valve will flex so that air can move around its perimeter into the mask port 415. When a patient exhales during the exhalation cycle, the air moving toward the umbrella valve 421 is blocked from moving back into the upper housing 401 but instead is directed outwardly towards the air expiratory port 419. Finally, a side port 425 is used to allow sampling or connection of a non-integrated manometer. A port cap 427 is used to cover the opening of the side port 425.

Figure 5:
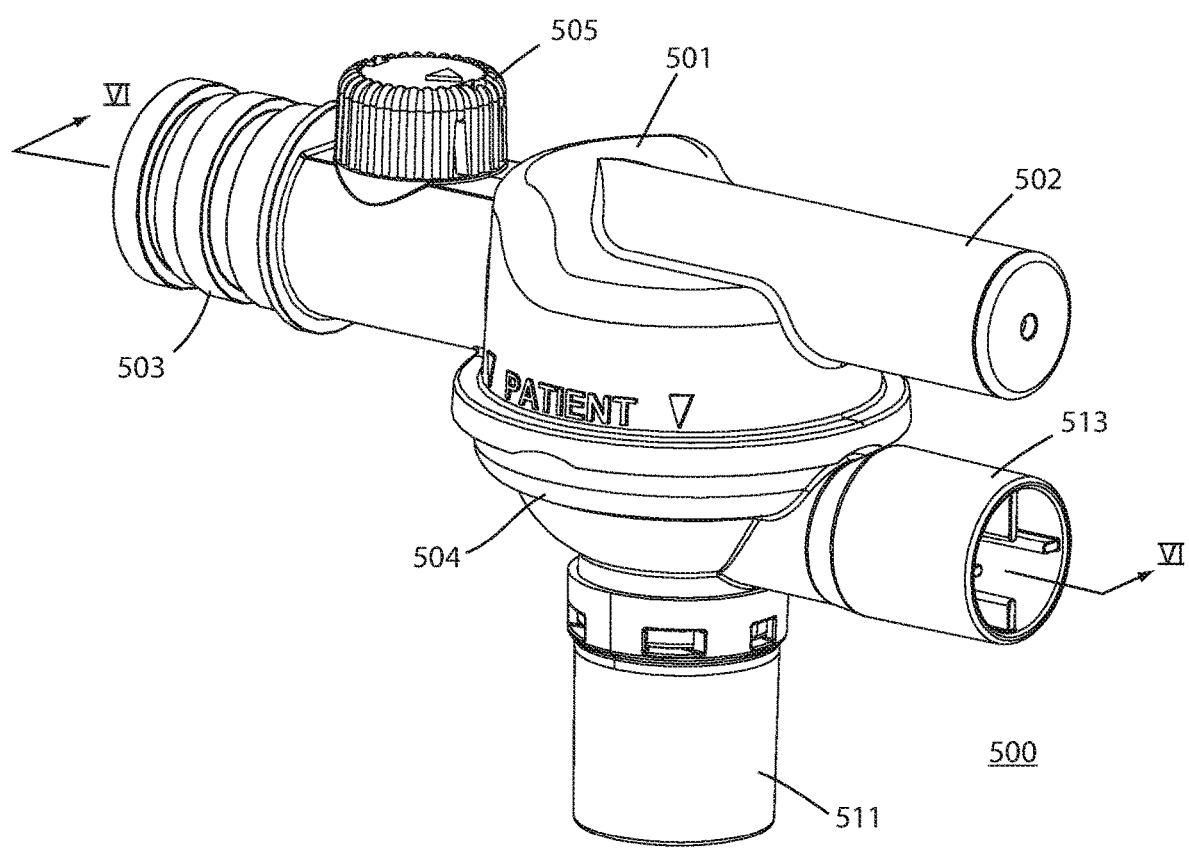
FIG. 5 is an elevated perspective view of the patient valve having an integrated linear manometer.

FIG. 5 is an elevated perspective view of the patient valve having an integrated linear manometer. Those skilled in the art will recognize that a manometer is an instrument for measuring the pressure acting on a column of fluid. When used in connection with a patient valve as described herein, the manometer works to measure both the patient's inhalation pressure and exhalation pressure. Inhalation pressure is the pressure of air used in pushing air from the ventilation bag though the valve and into the patient's lungs. Exhalation pressure is the pressure of the air removed or exerted by the patient when breathing out of the lungs. This pressure is typically measured in centimeters (cm) of water.

As seen in FIG. 5, the patient valve with integrated linear manometer 500 includes an upper housing 501, a bag port 503 and pressure relief valve 505. A linear manometer 502 is integrated into the top of the upper housing 501 opposite to the ventilator bag port 503. Although the linear monometer 502 is illustrated in the same plane as the bag port 503, those skilled in the art will recognize the linear manometer 502 can also be integrally formed at an angular relationship with the upper housing 501. For example, the linear manometer can be formed and/or adjusted at a 30-degree angle extending upwardly from the surface of the upper housing 501. This will make it easier for viewing by the clinician. As with the patient valve illustrated in FIG. 1, a lower housing 504 connects with the upper housing 501. The lower housing 504 includes a rotating mask port 511 and an air expiratory port 513. The operation of the umbrella valve and other components within the lower housing is as described with regard to FIG. 1.

Figure 6:
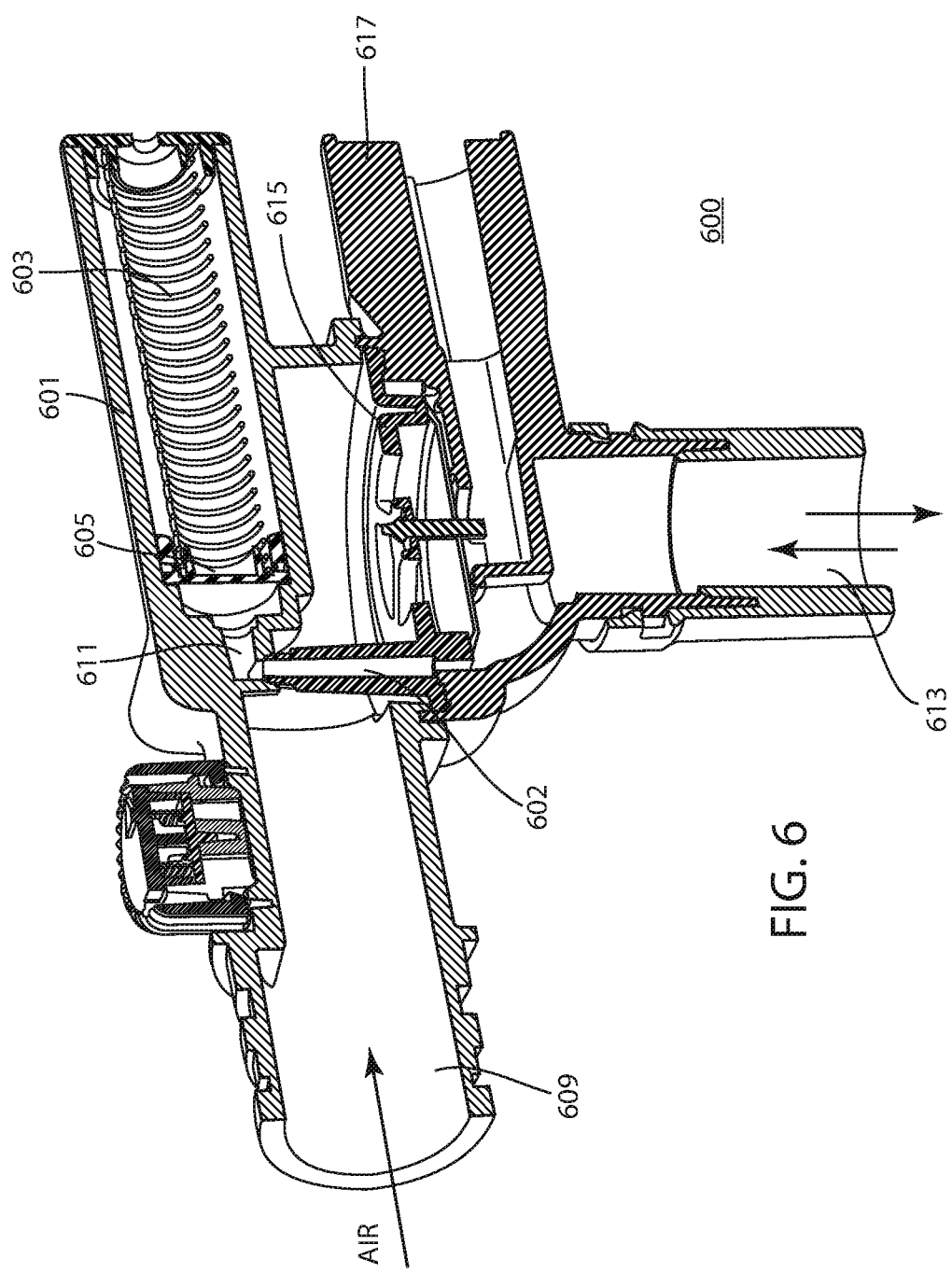
FIG. 6 is a cross-sectional view of the patient valve with integrated liner manometer taken through lines VI-VI of FIG. 5.

FIG. 6 is a cross-sectional view of the patient valve with integrated linear manometer taken through lines VI-VI of FIG. 5. The patient valve with linear manometer 600 illustrates the integrated linear manometer 601 having a spring 603 and piston 605 that moves according to pressure applied though various air channels. For example, during an inhalation cycle, air moving though the bag port 609 will move though manometer channels 602 and 611 which in-turn forces the piston 605 into the cylindrical housing indicating inhalation air pressure in cm $H_2O$. As described herein, during the exhalation cycle, air moving from the mask port 613 typically is blocked by an umbrella valve 615. Thus, the exhalation air moves through the exit port 617. However, a small amount of air moves from the mask port 613 and is forced though lower housing channel 602 into manometer channel 611 where the exhalation pressure can be measured in cm $H_2O$ on the linear manometer 601.

Figure 7:
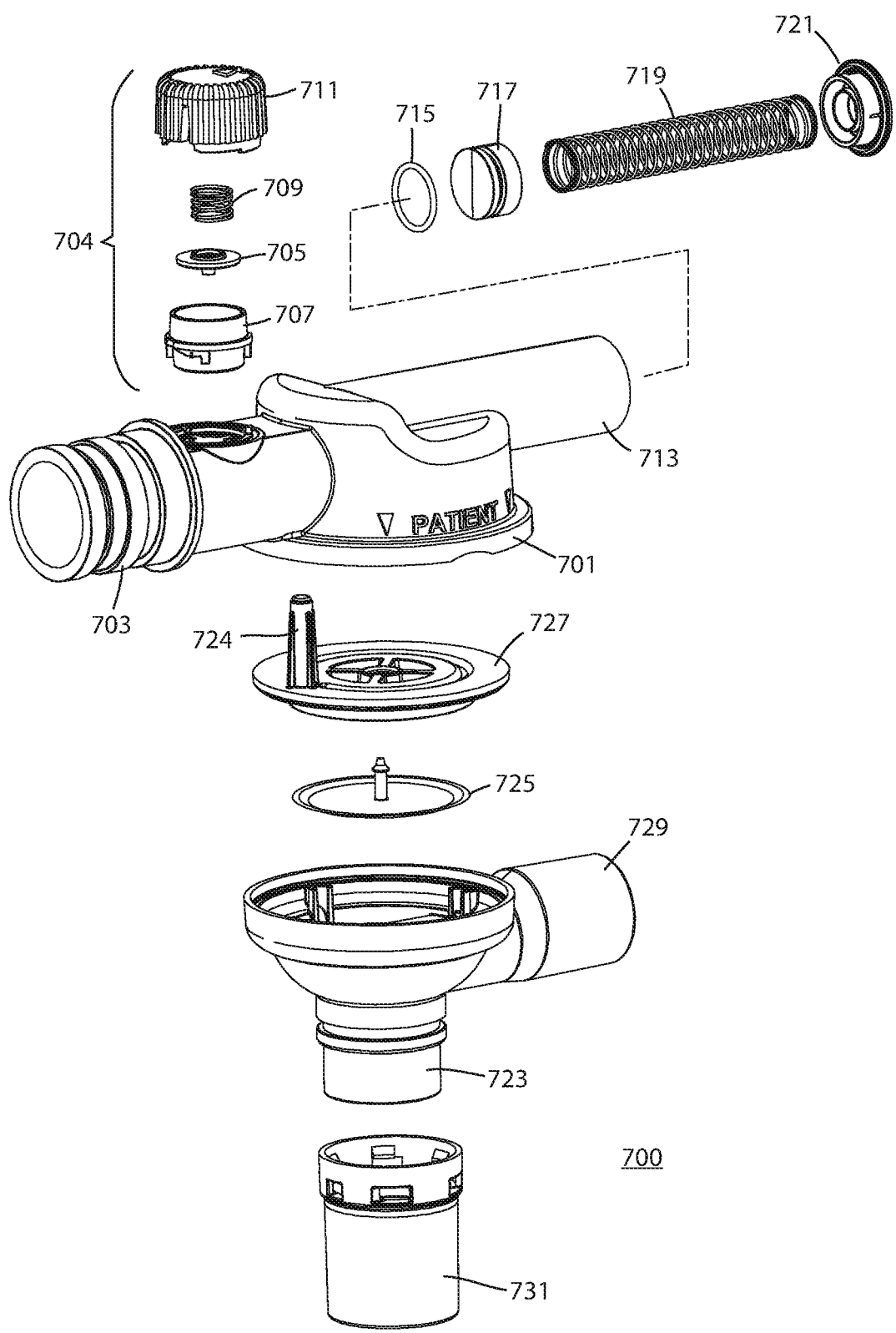
FIG. 7 is an exploded view of the patient valve having an integrated linear manometer shown in FIG. 5.

FIG. 7 is an exploded view of the patient valve 700 having an integrated linear manometer shown in FIG. 1. The patient valve 700 is shown having an upper housing 701 with bag port 703 and integrated linear manometer housing 713. Further as described herein, a pressure relief valve 704 is used in connection with the bag port 703 and includes a pop-off piston 705, pop-off body 707, pop-off spring 709 and pop-off cap 711. The linear manometer is used for measuring both inhalation pressure and exhalation pressure and includes an O-ring 715, piston 717, spring 719 and cap 721. These are held in compression within the manometer housing 713. The manometer housing typically includes a clear cover so that the piston 717 can be easily seen in relation to numbers or other indicia printed on the clear cover. Included within the lower housing 723 is an umbrella valve 725 and valve plate 727. The lower housing is formed so that the rotating mask port 731 connects with the lower housing. As described herein, the valve plate air channel 724 works to allow exhalation air from the mask port 723 to pressurize the manometer so that exhalation air pressure can also be read by the clinician.

Figure 8:
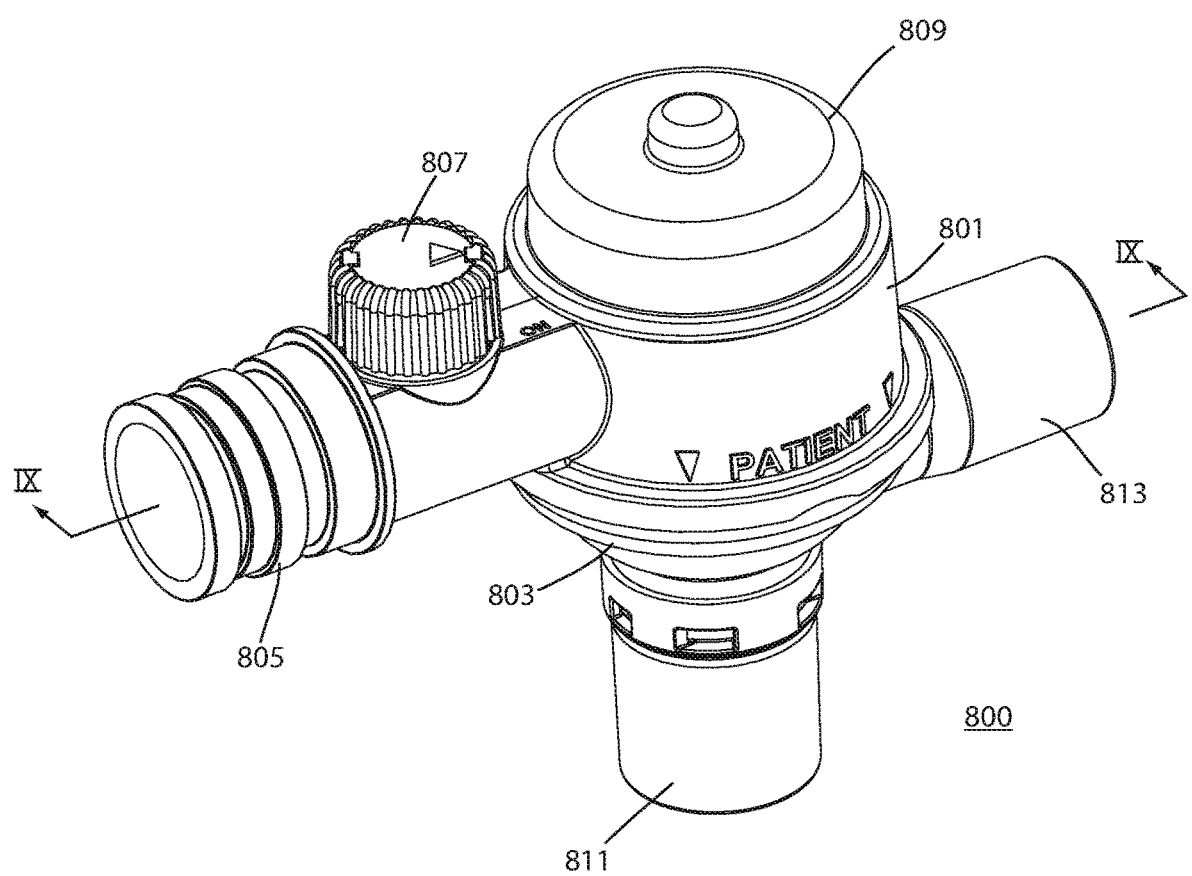
FIG. 8 is an elevated view of a patient valve having an integrated dial manometer.

FIG. 8 is an elevated view of a patient valve having an integrated dial manometer. Similar to the other embodiments are described herein, the valve having integrated dial manometer 800 includes an upper housing 801 and lower housing 803. The upper housing 801 includes a bag port 805, pressure relief valve 807 as well as a dial manometer 809. The dial manometer 809 is formed with and integrated into the upper housing 801. The lower housing 803 includes a rotating mask port 811 for connection to a patient mask as well as an expiratory vent port 813 for allowing exhalation air from the patient mask to escape to atmosphere.

Figure 9:
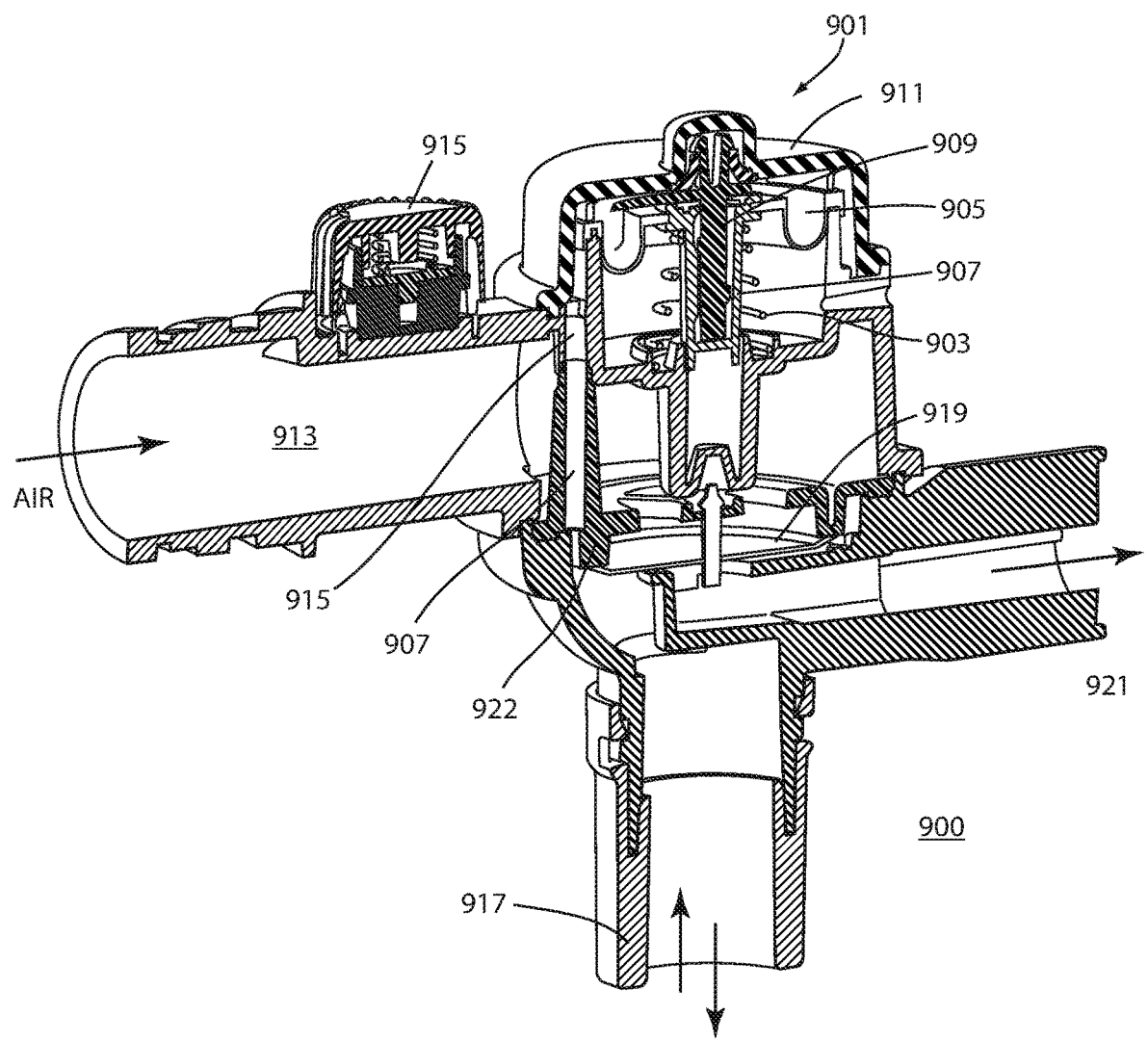
FIG. 9 is cross-sectional view of the patient valve with integrated dial manometer taken through lines IX-IX of FIG. 8.

FIG. 9 is cross-sectional view of the patient valve with integrated dial manometer taken through lines IX-IX of FIG. 8. The patient valve with dial manometer 900 includes a dial manometer 901 having a spring 903 that abuts against a dial diaphragm 905. A helix guide 907 is configured against the spring 903 and connects with pointer helix 909. A dial cover 911 is positioned above the pointer helix 907 so that a pointer's rotational position can be easily read on a circular dial scale.

In use, during the inhalation cycle, a small portion of air moves though the bag port 913, past the pressure relief port 914, into the upper housing through communications channels 907 and 915. This pressurizes the air inside the dial manometer 901 allowing the pressure to flex the dial diaphragm 905 which moves the helix guide 907 rectilinearly, which in-turn rotates the pointer helix 909. This will indicate the inhalation pressure of air from the bag port 913 to the mask port 917. During the patient's exhalation cycle, air moving from the mask port 917 is blocked by the umbrella valve 919 as described herein so the air is directed to the expiratory port 921. However, a small amount of air escapes though a lower housing air channel 907. The lower housing air channel 907 is integrated into a valve plate 922 for allowing exhalation air to move from the mask port 917 to upper channel 915. Thus, during the patient's exhalation breath, the pointer within the dial manometer 901 will rotate. This indicates to the clinician the amount of exhalation air pressure from the mask port 917 to the expiratory port 921, especially when used with a positive end-expiratory pressure (PEEP) attachment. The operation of the umbrella valve 919 and other components within the lower housing is as described with regard to FIG. 1.

Figure 10:
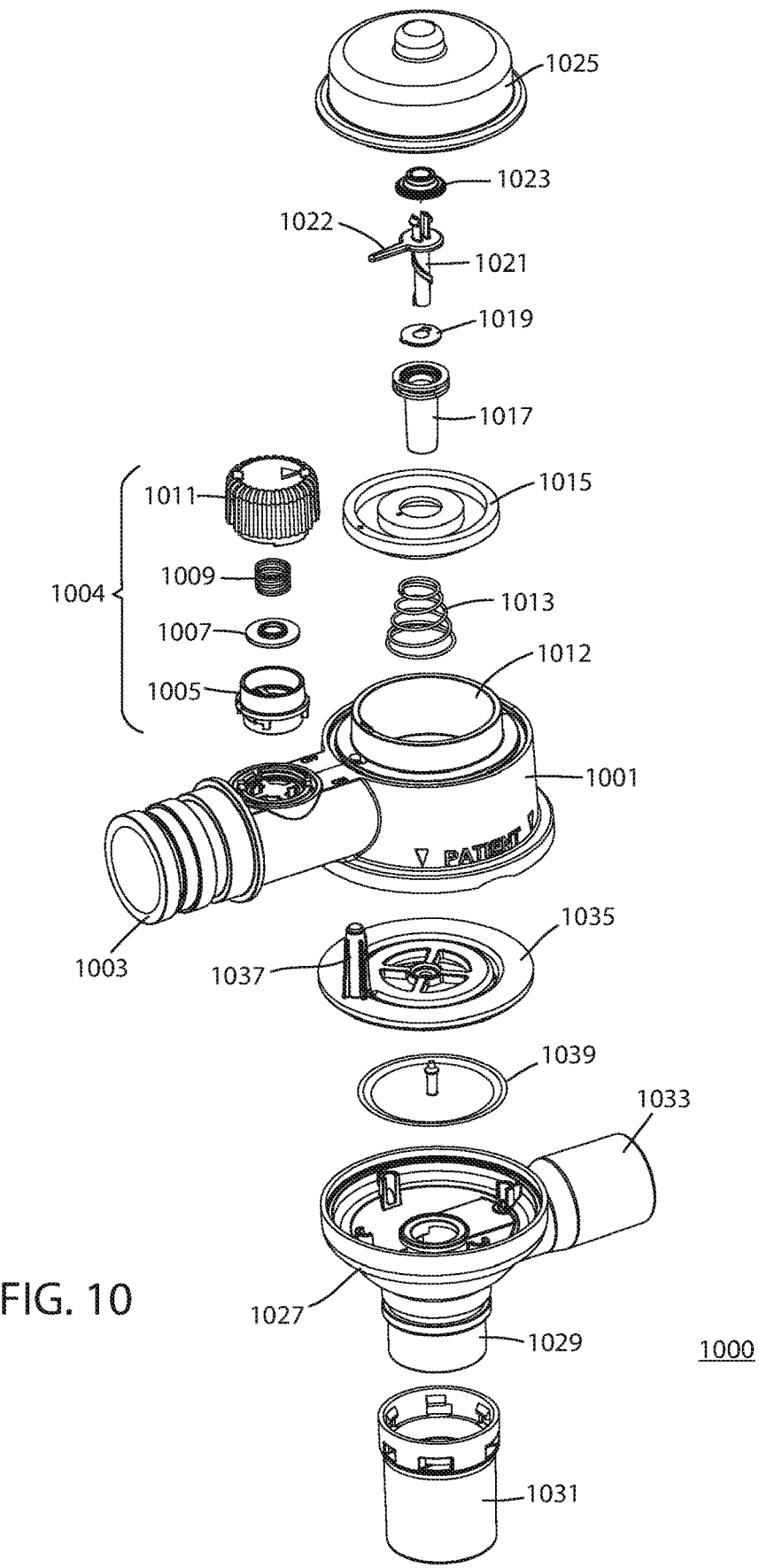
FIG. 10 is an exploded view of the patient valve having an integrated dial manometer shown in FIG. 8.

FIG. 10 is an exploded view of the patient valve having an integrated dial manometer shown in FIG. 8. The patient valve with integrated dial monomer 1000 includes a upper housing 1001 having a bag port 1003 and a pressure relief valve 1004. The relief valve 1004 is used in connection with the bag port 1003 and includes a pop-off body 1005, pop-off piston 1007, pop-off spring 1009 and pop-off cap 1011. The upper housing includes a dial flange 1012, spring 1013, a dial diaphragm 1015, and helix guide 1017. A key cap 1019 and pointer helix 1021 work in combination with the helix guide 1017 to provide rotational motion of the pointer 1022. A pointer helix retainer 1023 holds the pointer helix in a vertical position under the dial cover 1025. A lower housing includes the mask port 1029 used with a rotating mask port component 1031 for allowing a mask to rotate when attached. A expiratory port 1033 is used to vent the exhalation air from the patient to atmosphere.

Included within the lower housing 1027 is a valve plate 1035 that is used in combination with an umbrella valve 1039. As described in relation to the other embodiments, the lower housing is formed so that the expiratory port 1033 and rotating mask port 1031 connect with the lower housing. The valve plate air channel 1037 works to allow inhalation air and exhalation air to pressurize the dial manometer so that exhalation air pressure can also be read by the clinician.

Those skilled in the art may further recognize that phosphorescent materials can be used in each manometer indicator. For example, in FIG. 7, the piston in the integrated linear manometer patient valve can include phosphorescent materials to enhance the clinician's ability to see the piston in low light conditions. Similarly, in FIG. 10, the pointer helix in the integrated dial manometer patient valve may also include phosphorescent materials. Phosphorescent additives to the plastic resin will allow the molded parts associated with the piston, dial and pointer to glow in the dark. This may appeal to Emergency Medical personnel when using the product in twilight, darkness and/or low light conditions.

Thus, the present invention is directed a patient valve used with a manual resuscitator that includes an upper housing having a first port used in connection with a ventilator bag. A lower housing includes a second port for use with a patient mask and a third port for ventilating air from the second port to atmosphere. An air channel is integrally formed within the lower housing. An umbrella valve is configured within a valve plate inside the lower housing for controlling air movement between air ports. A linear or dial manometer is formed integrally within the upper housing and indicates both inhalation air pressure from the first port and exhalation pressure from the second port using the air channel.

In the foregoing specification, specific embodiments of the present invention have been described. However, one of ordinary skill in the art appreciates that various modifications and changes can be made without departing from the scope of the present invention as set forth in the claims below. Accordingly, the specification and figures are to be regarded in an illustrative rather than a restrictive sense, and all such modifications are intended to be included within the scope of present invention. The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

We claim:

1. A patient valve used with a manual resuscitator comprising:
    an upper housing having a first port used in connection with a ventilator bag;
    a lower housing having a second port used in connection with a patient mask and a third port for ventilating air from the second port to atmosphere;
    a manometer formed integrally within the upper housing;
    a valve plate including a first air channel and second air channel both integrally formed with the valve plate, the valve plate positioned between the upper housing and the lower housing such that the first air channel allows air to flow from the first port to the second port and the second air channel is configured to allow air to pressurize the manometer in the upper housing; and
    wherein the manometer indicates both inhalation air pressure from the first port and exhalation pressure from the second port through the second air channel in the valve plate.

2. A patient valve as in claim 1, further comprising an umbrella valve positioned within the lower housing for allowing air to flow from the first port to the second port during the patient inhalation and between the second port and third port during patient exhalation.

3. A patient valve as in claim 2, further wherein the umbrella valve prevents air from moving between the second port and first port during patient exhalation.

4. A patient valve as in claim 1, wherein the upper housing includes a pressure relief valve.

5. A patient valve as in claim 1, wherein the manometer is a linear manometer.

6. A patient valve as in claim 1, wherein the manometer is a dial manometer.

7. A patient valve as in claim 1, wherein the manometer includes phosphorescent materials to enhance visibility of components used in reading pressure values.

8. A patient valve used with a manual resuscitator comprising:
   an upper housing having a first port for connection to ventilator bag, and a lower housing having a second port for connection to a patient mask and a third port for an atmospheric vent;
   a valve plate including a first air channel and second air channel both integrally configured with the valve plate, the valve plate positioned between the upper housing and the lower housing such that the first air channel allows air to flow from the first port to the second port and the second air channel is configured to allow air to pressurize a manometer in the upper housing;
   the manometer for receiving air from the second air channel; and
   wherein the manometer is formed as an integral portion of the upper housing so to read both inhalation pressure from the first port and exhalation pressure from the second port.

9. A patient valve as in claim 8, further comprising an umbrella valve positioned within the lower housing for allowing air to flow from the first port to the second port during patient inhalation and between the second port and third port during patient exhalation.

10. A patient valve as in claim 9, wherein the valve plate is shaped to hold the umbrella valve therein.

11. A patient valve as in claim 9, further wherein the umbrella valve prevents air from moving between the second port and first port during patient exhalation.

12. A patient valve as in claim 8, wherein the upper housing includes a pressure relief valve.

13. A patient valve used with a manual resuscitator comprising:
   a housing having a first port for connection to ventilator bag, a second port for connection to a patient mask and a third port for an atmospheric vent;
   an umbrella valve positioned within the housing for allowing air to flow from the first port to the second port during the patient inhalation and between the second port and third port during patient exhalation;
   a valve plate having a first air channel and second air channel both integrally configured with the valve plate, the valve plate positioned in the housing; and
   a linear manometer for receiving inhalation air and exhalation air through the second air channel for determining both an inhalation pressure from the first port and an expiratory pressure from the second port; and
   wherein the first air channel allows air to flow from the first port to the second port and the second air channel is configured to allow air to pressurize the linear manometer in the housing.

\* \* \* \* \*